United States Patent [19]
LeGrow et al.

[11] Patent Number: 5,847,179
[45] Date of Patent: Dec. 8, 1998

[54] HIGH PURITY ALKOXYTRIMETHYLSILANE FLUIDS

[75] Inventors: Gary E. LeGrow, Newberry; William I. Latham, III, Gainesville, both of Fla.

[73] Assignee: PCR, Inc., Gainesville, Fla.

[21] Appl. No.: 947,523

[22] Filed: Oct. 2, 1997

[51] Int. Cl.[6] ................................. C07F 7/08; C07F 7/18
[52] U.S. Cl. .................... 556/482; 556/470; 556/471; 424/611; 424/401; 514/844; 514/873
[58] Field of Search ..................... 556/470, 471, 556/482; 514/844, 873; 424/64, 401

[56] References Cited

U.S. PATENT DOCUMENTS

| | | | |
|---|---|---|---|
| 4,400,509 | 8/1983 | Bruynes et al. | 544/315 |
| 4,500,725 | 2/1985 | Yemoto et al. | 556/482 |
| 5,126,136 | 6/1992 | Merat et al. | 424/401 |
| 5,157,139 | 10/1992 | Legrow et al. | 556/470 |
| 5,183,914 | 2/1993 | Yeh et al. | 556/470 X |
| 5,326,557 | 7/1994 | Glover et al. | 424/78.03 |
| 5,340,570 | 8/1994 | Wong et al. | 424/71 |
| 5,435,996 | 7/1995 | Glover et al. | 424/78.03 |
| 5,543,540 | 8/1996 | Schwindeman | 556/466 |

FOREIGN PATENT DOCUMENTS 9414404  7/1994  WIPO .

*Primary Examiner*—Paul F. Shaver
*Attorney, Agent, or Firm*—Hedman, Gibson, Costigan, P.C.

[57] ABSTRACT

The invention provides high purity alkoxytrimethylsilane fluids of the general formula $ROSiMe_3$ wherein Me is methyl and R is a monovalent aliphatic hydrocarbon substituent which ranges from 14 to about 20 carbons, the fluid being substantially free of organic and inorganic contaminants, wherein the alkoxytrimethylsilanes are produced by a novel process, and can be readily incorporated into cosmetic formulations containing organic components without heating and provide improved sensory characteristics compared to those provided by the corresponding alcohols.

19 Claims, No Drawings

HIGH PURITY ALKOXYTRIMETHYLSILANE FLUIDS

FIELD OF THE INVENTION

The present invention relates to high purity alkoxytrimethylsilane fluids and a method for their preparation. More specifically, the present invention relates to alkoxytrimethylsilane fluids prepared from solid long chain aliphatic alcohols, and the use of the alkoxytrimethylsilane fluids in cosmetic formulations.

BACKGROUND OF THE PRESENT INVENTION

A wide range of long chain aliphatic alcohols are used in cosmetic formulations, including skin care products, because of some of the inherent desirable characteristics of these materials including occlusivity, substantivity, and water repellency. Long chain aliphatic alcohols, possessing these characteristics, typically have carbon chain lengths ranging from 12 upwards to more than 20 carbon atoms. When pure, all of these alcohols are solids at room temperature. As the carbon chain length increases, the melting point of the compound also increases, as shown in TABLE I below.

TABLE I

| | | |
|---|---|---|
| Lauryl alcohol | $CH_3$—$(CH_2)_{10}$—$CH_2OH$ | MP = 22–26° C. |
| Myristyl alcohol | $CH_3$—$(CH_2)_{12}$—$CH_2OH$ | MP = 38–40° C. |
| Cetyl alcohol | $CH_3$—$(CH_2)_{14}$—$CH_2OH$ | MP = 54–56° C. |
| Stearyl alcohol | $CH_3$—$(CH_2)_{16}$—$CH_2OH$ | MP = 60–61° C. |
| Arachidyl alcohol | $CH_3$—$(CH_2)_{18}$—$CH_2OH$ | MP = 64–66° C. |
| Behenyl alcohol | $CH_3$—$(CH_2)_{20}$—$CH_2OH$ | MP = 71–72° C. |

It is also known in the art that occlusivity, substantivity, and water repellency characteristics improve with increasing chain length of the aliphatic alcohol. Because of the increased melting point of the longer chain aliphatic alcohols, more difficulty is encountered when formulating cosmetic products with these materials. Frequently, the higher melting longer chain aliphatic alcohols are required to be melted, such as in a hot room, and then formulations are prepared while these materials are maintained in a molten state. The requirement of performing this melting step represents a significant disadvantage to the use of the alcohols in formulating cosmetic or other personal care products. It would therefore represent a notable advance in the state of the art if a composition which is useful in providing the beneficial characteristics of the long chain alcohol could be developed which did not also possess the drawback of requiring melting prior to formulation.

Trimethylsilylation is a known process in which a trimethylsilyl group is introduced into an organic molecule by substitution of at least one active hydrogen atom. It is known in the art that active hydrogen containing organic compounds can be trimethylsilylated by certain classes of organosilicon compounds. For example, U.S. Pat. No. 5,157,139 ("the '139 patent") discloses silylating alcohols and ethers with a silylating agent and an inorganic acid catalyst. In one example of the '139 patent stearyl alcohol is trimethylsilylated by hexamethyldisilazane using sulfuric acid as the catalyst. In many of the other materials discussed for silylation in the '139 patent, the acid can only be removed with great difficulty due to the high solubility in the polyether molecules produced, thus making it very difficult to obtain a high purity product. Additionally, the use of the mineral acids taught in the '139 patent proceeds at a slow rate, making the process relatively uneconomical commercially.

The present invention solves the problems of the prior art by providing a rapid catalytic process for the trimethylsilylation of long chain alcohols from which pure, clear colorless, liquid, long chain alkoxytrimethylsilanes can easily be obtained, and can easily be formulated into a cosmetic formulation.

SUMMARY OF THE INVENTION

The present invention provides high purity clear colorless liquid (at and below skin temperature) long chain alkoxytrimethylsilanes of the general formula R—O—SiMe$_3$ where Me is methyl and R is a straight chain or branched chain monovalent hydrocarbon substituent with from 14 to about 20 or more carbon atoms wherein the alkoxytrimethylsilane fluid is substantially free of organic and inorganic compounds.

The present invention also provides a method for rapidly producing high purity, clear, colorless, liquid (at and below skin temperature), long chain alkoxytrimethylsilanes, the process comprising the steps of (a) melting a long straight chain or branched aliphatic solid alcohol; (b) catalyzing the liquid alcohol with an effective amount of an organic superacid; (c) reacting the alcohol with a stoichiometric excess of a trimethylsilylating agent; (d) removing residual trimethylsilylating agent and reaction by-product, under vacuum, from the product; (e) neutralizing the mixture with an anhydrous base; and (f) filtering insoluble salts from the product.

Careful attention must be paid to step (c) wherein the trimethylsilylating agent is added to the molten alcohol, catalyzed with the organic superacid, to avoid an uncontrollable reaction.

DETAILED DESCRIPTION OF THE PRESENT INVENTION

As used throughout the present specification and claims the phrase "substantially free" means at least 95% pure, and more preferably at least 97% pure.

The present invention provides high purity, clear, colorless, liquid (at and below skin temperature), long chain alkoxytrimethylsilanes of the general formula:

RO—SiMe$_3$ wherein Me is methyl and R is a straight chain or branched chain monovalent hydrocarbon substituent with from 14 to about 20 or more carbon atoms wherein the alkoxytrimethylsilane fluid is substantially free of organic and inorganic compounds.

The present invention also provides a method for producing high purity clear colorless liquid (at and below skin temperature) long chain alkoxytrimethylsilane, the process comprising the steps of (a) melting a long straight chain or branched chain aliphatic solid alcohol; (b) catalyzing the liquid alcohol with an organic superacid; (c) reacting the alcohol with a stoichiometric excess of a trimethylsilylating agent (d) removing residual hexamethyldisilazane and ammonia, under vacuum, from the product; (e) neutralizing the mixture with an anhydrous base; and (f) filtering insoluble salts from the product.

The organic superacids useful in the practice of the present invention are typically those having a pKa of at least about −14 and having an organic group. Thus, the superacids useful in the practice of the present invention are on the order of a million times more acidic than the strongest mineral acids. These superacids are well known to those of ordinary skill in the art and are available commercially or can be produced by methods also known to those skilled in the art. Exemplary superacids useful in accordance with the present invention include but are not limited to trifluoromethanesulfonic acid, pentafluorophenylsulfonic acid, trifluoroacetic acid, pentafluorophenylacetic acid, pentafluoropropionic acid and mixtures of any of the foregoing. Especially preferred is trifluoromethanesulfonic acid.

Any effective amount of the organic superacid may be employed sufficient to catalyze the trimethylsilylation reaction, such as from about 20 to about 200 ppm by weight based on the amount of alcohol.

The trimethylsilylating agents useful in the practice of the present invention include any compound which is capable of reacting with a long chain alcohol to introduce a trimethylsilyl group into the alcohol in substitution for active hydrogen. Trimethylsilylating agents are well known to those skilled in the art and are available commercially or may be produced by known methods. Exemplary trimethylsilylating agents useful in the practice of the present invention include, but are not limited to, hexamethyldisilazane ($(Me_3Si)_2NH$), hexamethyldisilthiane ($(Me_3Si)_2S$), bis(trimethylsilyl)acetamide ($MeCON(SiMe_3)_2$), bis(trimethylsilyl)urea ($(Me_3SiNH)_2C=O$), trimethylsilyldimethylamine ($Me_3SiNMe_2$), trimethylsilylmethane sulfonate ($Me_3SiOSO_2Me$) and mixtures of any of the foregoing. Preferred are hexamethyldisilazane and trimethylsilyldimethylamine which produce readily removable gaseous by-products. Especially preferred is hexamethyldisilazane.

The long straight chain or branched chain aliphatic solid alcohol are those of the formula R—OH where R is a straight chain or branched chain monovalent hydrocarbon substituent with from 14 to about 20 or more carbon atoms. These are commercially available or may be produced by methods known to those of ordinary skill in the art. The preferred alcohols for use in the practice of the present invention are myristyl alcohol, cetyl alcohol, stearyl alcohol, arachidyl alcohol, behenyl alcohol and mixtures of any of the foregoing. Preferred are cetyl alcohol, stearyl alcohol and mixtures thereof.

Similarly, the anhydrous base, which may be any of the known anhydrous bases, such as, but not limited to calcium oxide, magnesium oxide, calcium carbonate, magnesium carbonate or mixtures thereof, are also commercially available or may be produced by methods known to those of ordinary skill in the art. In preferred embodiments, substantially pure to completely pure reagents are employed in the process of the present invention.

Step (a) of the process of the present invention, melting of the long straight chain or branched chain aliphatic solid alcohol, may be carried out by slowly heating any of the wax-like alcohols in a hot room, avoiding localized overheating, to a temperature of about 10° C. or more above its melting point. This procedure of melting will reduce thermal decomposition of the alcohol, although other melting procedures may be employed without departing from the scope of the present invention.

Step (b) of the process of the present invention, involves transferring the molten alcohol to a stirred reactor, maintaining the temperature at about 10° C. or more above the melting point of the alcohol, and catalyzing the molten alcohol with an organic superacid.

Step (c) involves adding the stoichiometric excess of trimethylsilylating agent to the reactor at such a rate as to avoid an uncontrollable exotherm, and frothing due to an excessive rate of formation of reaction by-product, such as ammonia in the case of hexamethyldisilazane. The reaction preferably takes place in an inert, essentially anhydrous atmosphere. By inert is meant that the reaction is carried out under a blanket of inert gas such as argon, nitrogen or helium. By essentially anhydrous is meant that the reaction is preferably carried out in an absolutely anhydrous atmosphere but minute amounts of moisture can be tolerated. The temperature of the reaction should be maintained at a temperature at least about 10° C. above the melting point of the alcohol reactant, preferably up to about 100° C.

Step (d) is directed toward removal of the reaction by-product and the excess trimethylsilylating agent under vacuum, leaving the product substantially free of organic and inorganic compounds.

Step (e) involves neutralization of the trifluoromethanesulfonic acid with an anhydrous base, such as sodium bicarbonate, calcium oxide, magnesium oxide, calcium carbonate, magnesium carbonate, mixtures thereof and the like to form a salt insoluble in the product.

Step (f) is directed to removal of the salt from the product by filtration, preferably under an inert essentially anhydrous atmosphere.

The liquid high purity alkoxytrimethylsilanes produced in accordance with the present invention have the advantage of simple mixing with other organic ingredients at room temperature when producing formulated products without the need for heating associated with the alcohol precursors. Further, surprisingly, the alkoxytrimethysilanes of the present invention exhibit sensory characteristics which are equivalent or improved as compared to the corresponding long chain alcohol. Thus, the liquid high purity alkoxytrimethylsilanes of the present invention can be formulated into cosmetic preparations, such as in skin and hair conditioning products, moisturizers, lotions and cleansers by substituting all or a part of the long chain alcohol components of these preparations with the alkoxytrimethylsilanes of the present invention.

DESCRIPTION OF THE PREFERRED EMBODIMENTS

The following examples illustrate the present invention. They are not to be construed to limit the scope of the appended claims in any manner whatsoever.

EXAMPLE 1

To a 4 necked 500 ml round bottomed flask equipped with a mechanical stirrer, heating mantle, two foot condenser, addition funnel (with dip tube for sub-surface delivery) and a thermometer was added 168.0 g (0.62 mole) of solid stearyl alcohol. The contents of the flask were heated, melting the alcohol, forming a liquid. To this liquid alcohol was added 52.65 g (0.325 mole) of hexamethyldisilazane via the addition funnel. On complete addition, a clear liquid solution of the two reagents, at 90° C., was present in the flask. Very little reaction had occurred at this point, based upon the small amount of evolution of ammonia gas. Two drops of trifluoromethanesulfonic acid were then added to the flask through the condenser. Gas evolution and frothing occurred immediately and most of the contents of the flask were lost through the condenser. A gas chromatography analysis of a sample of the liquid remaining in the flask showed the liquid to be 96.6% pure stearoxytrimethylsilane. This material remained as a clear, colorless liquid at room temperature. This example is included to demonstrate the catalytic effect of trifluoromethanesulfonic acid on this reaction and not to demonstrate the best mode of carrying out the reaction.

EXAMPLE 2

To a 4 necked 500 ml round bottomed flask equipped with a mechanical stirrer, heating mantle, two foot condenser, addition funnel (with dip tube for sub-surface delivery) and a thermometer was added 168.0 g (0.62 mole) of solid stearyl alcohol. The contents of the flask were heated, melting the alcohol, forming a liquid. To this liquid alcohol was added 4 drops of trifluoromethanesulfonic acid. To this mixture was added (sub-surface) 52.65 g (0.325 mole) of hexamethyldisilazane through the addition funnel. Ammonia evolution began immediately on addition of the hexamethyldisilazane. The addition was completed in 30 minutes. The mixture was stirred for 6 hours. A gas chromatographic analysis of the crude product at this point identified liquid stearoxytrimethylsilane at 91.5% purity with the major contaminant being unreacted hexamethyldisilazane. Ammonia and hexamethyldisilazane were then removed from the crude product by stripping volatiles under reduced pressure. To the product was then added 5 g. of calcium carbonate with stirring, followed by filtration under a nitrogen blanket. A gas chromatographic analysis of the product at this point identified stearoxytrimethylsilane at 98.3% purity with the major contaminant being stearyl alcohol, presumably formed by hydrolysis of stearoxytrimethylsilane during the work up.

EXAMPLE 3

To a 4 necked 250 ml round bottomed flask equipped with a mechanical stirrer, heating mantle, one foot condenser, addition funnel (with dip tube for sub-surface delivery) and a thermometer was added 60.0 g (0.28 mole) of solid myristyl alcohol. The contents of the flask were heated, melting the alcohol, forming a liquid. To this liquid alcohol was added 60 µl of trifluoromethanesulfonic acid. To this mixture was added (sub-surface) 25.0 g (0.155 mole) of hexamethyldisilazane through the addition funnel. Ammonia evolution began immediately on addition of the hexamethyldisilazane. The addition was completed in 15 minutes. The mixture was stirred for 3 hours at 70° C. A gas chromatographic analysis of the crude product at this point identified myristoxytrimethylsilane at 93.3% purity with the major contaminant being unreacted hexamethyldisilazane. Ammonia and hexamethyldisilazane were then removed from the crude product by stripping volatiles under reduced pressure. To the product was added 5 g. of sodium bicarbonate with stirring, followed by filtration to remove the salt and adsorbed chemicals. A gas chromatographic analysis of the product at this point identified liquid myristoxytrimethylsilane at 97.8% purity with a refractive index of 1.4303 (25° C.), the major contaminant being myristyl alcohol, presumably formed by hydrolysis of myristoxytrimethylsilane during the work up.

EXAMPLE 4

To a 4 necked 250 ml round bottomed flask equipped with a mechanical stirrer, heating mantle, one foot condenser, addition funnel (with dip tube for sub-surface delivery) and a thermometer was added 121.0 g (0.50 mole) of solid cetyl alcohol. The contents of the flask were heated, melting the alcohol, forming a liquid. To this liquid alcohol was added 1 drop of trifluoromethanesulfonic acid. To this mixture was added (sub-surface) 48.5 g (0.30 mole) of hexamethyldisilazane through the addition funnel. Ammonia evolution began immediately on addition of the hexamethyldisilazane. The addition was completed in 15 minutes. The mixture was stirred overnight at 65° C. A gas chromatographic analysis of the crude product at this point identified cetoxytrimethylsilane at 95.7% purity with the major contaminant being unreacted hexamethyldisilazane. Hexamethyldisilazane was then removed from the crude product by stripping volatiles under reduced pressure. To the product was added 5 g. of sodium bicarbonate with stirring, followed by filtration to remove the salt and adsorbed chemicals. A gas chromatographic analysis of the product at this point identified liquid cetoxytrimethylsilane at 98.7% purity with a refractive index of 1.4350 (25° C.), the major contaminant being cetyl alcohol, presumably formed by hydrolysis of cetoxytrimethylsilane during the work up.

EXAMPLE 5

To a 4 necked 250 ml round bottomed flask equipped with a mechanical stirrer, heating mantle, one foot condenser, addition funnel (with dip tube for sub-surface delivery) and a thermometer was added 100.0 g (0.34 mole) of solid arachidyl alcohol. The contents of the flask were heated, melting the alcohol, forming a liquid. To this liquid alcohol was added 2 drops of trifluoromethanesulfonic acid. To this mixture was added (sub-surface) 41.1 g (0.255 mole) of hexamethyldisilazane through the addition funnel. Ammonia evolution began immediately on addition of the hexamethyldisilazane. The addition was completed in 30 minutes. The mixture was stirred for 3 hours at 80° C. A gas chromatographic analysis of the crude product at this point identified arachidoxytrimethylsilane at 87.7% purity with the major contaminant being 10.7% unreacted hexamethyldisilazane. Hexamethyldisilazane was then removed from the crude product by stripping volatiles under reduced pressure. To the product was then added 5 g. of sodium bicarbonate with stirring, followed by filtration to remove the salt and adsorbed chemicals. A gas chromatographic analysis of the product at this point identified arachidoxytrimethylsilane at 99.1% purity, a soft wax with a softening point of 24.5° C.

EXAMPLE 6

To a 4 necked 250 ml round bottomed flask equipped with a mechanical stirrer, heating mantle, one foot condenser, addition funnel (with dip tube for sub-surface delivery) and a thermometer was added 78.0 g (0.24 mole) of solid behenyl alcohol. The contents of the flask were heated, melting the alcohol, forming a liquid. To this liquid alcohol was added 1 drop of trifluoromethanesulfonic acid. To this mixture was added (sub-surface) 22.0 g (0.136 mole) of hexamethyldisilazane through the addition funnel. Ammonia evolution began immediately on addition of the hexamethyldisilazane. The addition was completed in 15 minutes. The mixture was stirred overnight at 40° C. Hexamethyldisilazane was then removed from the crude product by stripping volatiles under reduced pressure. To the product was added 5 g. of sodium bicarbonate with stirring at 40° C., followed by filtration to remove the salt and adsorbed chemicals. A gas chromatographic analysis of the product at this point identified behenoxytrimethylsilane at 97.6% purity, a soft waxy solid with a softening point of 32° C.

EXAMPLE 7

All of the above alkoxytrimethylsilanes were tested for traces of acids or bases and found to be neutral using pH paper. The melting points of the liquid products above were also determined using a sub-ambient melting point apparatus. The melting points of all of the above products are shown below in Table II and compared to the melting points of the corresponding alcohols, from which they are derived.

TABLE II

Melting Point (°C.) of waxy alcohols and their Trimethylsilyl derivatives

| Alcohol | Melting point of Alcohol | Melting Point of Trimethylsilyl derivative |
| --- | --- | --- |
| Myristyl | 38–40° C. | −7° C. |
| Cetyl | 54–56° C. | 7° C. |
| Stearyl | 60–61° C. | 16° C. |
| Arachidyl | 64–66° C. | 24.5° C. |
| Behenyl | 71–72° C. | 32° C. |

EXAMPLE 8

Sensory characterization was performed on 3 pure alkoxytrimethylsilanes, and a commercially available mixture of stearoxytrimethylsilane and stearyl alcohol, DC-580 manufactured by Dow Corning Corporation, Midland, Mich., according to the protocol of ASTM Method E 1490-2, entitled "Sensory Evaluation of Materials and Products." The number of trained test panelists was 10.

Table III shows the average comparative sensory profiles for these three compounds and the commercially available mixture.

TABLE III

Comparative Sensory Profiles for Alkoxytrimethylsilanes

| Characteristic | A | B | C | D* |
| --- | --- | --- | --- | --- |
| Stickiness | 0.7 | 1.0 | 4.4 | 2.0 |
| Wetness | 8.4 | 7.9 | 3.9 | 2.5 |
| Spreadability | 9.1 | 8.8 | 3.5 | 4.6 |
| Gloss | 7.8 | 7.1 | 2.6 | 3.0 |
| Slipperiness | 9.1 | 8.4 | 5.6 | 7.0 |
| Tackiness | 9.4 | 9.1 | 6.2 | 9.8 |
| Smoothness | 8.6 | 8.0 | 5.3 | 8.0 |
| Residue | 3.2 | 4.0 | 8.5 | 6.0 |
| Oiliness | 5.8 | 6.0 | 2.7 | 1.8 |
| Greasiness | 3.1 | 2.7 | 2.0 | 3.3 |
| Waxiness | 1.6 | 1.0 | 7.4 | 8.0 |

A = Stearoxytrimethylsilane, >99% pure
B = Cetoxytrimethylsilane, >98.7% pure
C = Behenoxytrimethylsilane, >97.6% pure
D = Dow Corning DC-580 Wax
* = Comparative Example Within the experimental error associated with this type of testing, it can be concluded that the sensory profiles of the liquid alkoxysilanes, cetoxytrimethylsilane and stearoxytrimethylsilane, are significantly and statistically different than the profile of the commercially available mixture. The differences most notable include increased wetness, spreadability, gloss and oiliness, and decreased residue and waxiness.

Many variations of the present invention will suggest themselves to those skilled in the art in light of the above-detailed description. For example, a mixture of two or more solid long straight chain or branched chain aliphatic solid alcohols could be trimethylsilylated simultaneously, forming a mixture of liquid high purity alkoxytrimethylsilanes substantially free of organic and inorganic compounds. Other known organic superacids or trimethylsilylating agents may be employed in producing the compositions of the present invention. All such obvious modifications are within the full intended scope of the appended claims.

All of the above-referenced patents, publications and test methods are hereby incorporated by reference.

We claim:

1. A process for the production of a high purity liquid alkoxytrimethylsilane of the general formula:

$$ROSiMe_3$$

wherein Me is methyl, and R is a monovalent aliphatic hydrocarbon substituent having from about 14 to about 20 or more carbon atoms, said fluid being substantially free of organic and inorganic compounds, said process comprising the steps of:

(a) melting a solid alcohol of the general formula R—OH wherein R is as defined above;

(b) catalyzing said molten alcohol with an effective amount of an organic superacid;

(c) reacting said catalyzed molten alcohol at a temperature ranging from about 10° C. above the melting point of said alcohol to about 100° C. in an inert, essentially anhydrous atmosphere with at least a stoichiometric equivalent amount of a trimethylsilylating agent;

(d) removing any reaction by-product and excess trimethylsilylating agent;

(e) neutralizing the organic superacid catalyst with an excess of an anhydrous base; and (f) removing salts from said liquid alkoxytrimethylsilane by filtration.

2. A process as defined in claim 1 wherein said molten alcohol is selected from cetyl alcohol, stearyl alcohol and mixtures of any of the foregoing.

3. A process as defined in claim 2 wherein said molten alcohol comprises stearyl alcohol.

4. A process as defined in claim 3 wherein said molten alcohol comprises cetyl alcohol.

5. A process as defined in claim 1 wherein said organic superacid is selected from the group consisting of trifluoromethanesulfonic acid, pentafluorophenylsulfonic acid, trifluoroacetic acid, pentafluorophenylacetic acid, pentafluoropropionic acid and mixtures of any of the foregoing.

6. A process as defined in claim 5 wherein said organic superacid comprises trifluoromethanesulfonic acid.

7. A process as defined in claim 6 where said effective amount of organic superacid comprises from about 20 to about 200 ppm of trifluoromethanesulfonic acid.

8. A process as defined in claim 1 wherein said trimethylsilylating agent is selected from the group consisting of hexamethyldisilazane, hexamethyldisilthiane, bis(trimethylsilyl)acetamide, bis(trimethylsilyl)urea, trimethylsilyldimethylamine, trimethylsilylmethane sulfonate and mixtures of any of the foregoing.

9. A process as defined in claim 8 wherein said trimethylsilylating agent is selected from the group consisting of hexamethyldisilazane, trimethylsilyldimethylamine and mixtures of any of the foregoing.

10. A process as defined in claim 9 wherein said trimethylsilylating agent comprises hexamethyldisilazane.

11. The process of claim 1 wherein said anhydrous base is selected from the group consisting of sodium bicarbonate, magnesium oxide, calcium oxide, magnesium carbonate, calcium carbonate and mixtures of any of the foregoing.

12. A high purity liquid alkoxytrimethylsilane of the general formula:

$$ROSiMe_3$$

wherein Me is methyl, and R is a monovalent aliphatic hydrocarbon substituent having from about 14 to about 20 or more carbon atoms, said fluid being substantially free of organic and inorganic compounds and produced by the process as defined in claim 1.

13. A high purity, neutral, colorless, and odorless liquid alkoxytrimethylsilane of the general formula:

ROSiMe$_3$ wherein Me is methyl, and R is a monovalent aliphatic hydrocarbon substitutent having from about 14 to about 20 or more carbon atoms, said fluid being substantially free of organic and inorganic compounds.

14. A high purity liquid alkoxytrimethylsilane as defined in claim 13 wherein R is a monovalent aliphatic hydrocarbon substituent having from 16 to about 18 carbon atoms.

15. A high purity liquid alkoxytrimethylsilane as defined in claim 13 wherein R is a monovalent aliphatic hydrocarbon substituent having 16 carbon atoms.

16. A high purity liquid alkoxytrimethylsilane as defined in claim 13 wherein R is a monovalent aliphatic hydrocarbon substituent having 18 carbon atoms.

17. A high purity liquid cetoxytrimethylsilane as defined in claim 15 having a purity greater than about 98%.

18. A high purity liquid stearoxytrimethylsilane as defined in claim 16 having a purity greater than about 98%.

19. A cosmetic preparation comprising a high purity liquid alkoxytrimethylsilane possessing improved wetness, improved spreadability, improved gloss, improved residue and improved waxiness, as compared to its precursor solid alcohol, R'—OH wherein R' is a monovalent aliphatic hydrocarbon substituent with 16 to about 18 carbons produced by the process as defined in claim 1.

* * * * *